United States Patent [19]

Luhr et al.

[11] Patent Number: 5,129,903
[45] Date of Patent: Jul. 14, 1992

[54] BONE PLATE

[76] Inventors: Hans-Georg Luhr; Hans E. Harder, both of Pfizer Inc., 235 E. 42nd St., New York, N.Y. 10017-5755

[21] Appl. No.: 364,045

[22] Filed: Jun. 9, 1989

[30] Foreign Application Priority Data

Jun. 18, 1988 [DE] Fed. Rep. of Germany ... 8807909[U]

[51] Int. Cl.⁵ .............................................. A61B 17/58
[52] U.S. Cl. ........................................ 606/71; 606/69
[58] Field of Search ............... 128/92 YP, 92 YL; 606/69-71, 60, 72

[56] References Cited

U.S. PATENT DOCUMENTS

| 2,406,832 | 9/1946 | Hardinge | 606/71 |
| 2,443,363 | 6/1948 | Townsend et al. | 606/71 |
| 3,604,414 | 9/1971 | Borges | 606/71 X |

FOREIGN PATENT DOCUMENTS

| 2938202 | 4/1981 | Fed. Rep. of Germany . | |
| 2437752 | 3/1983 | Fed. Rep. of Germany . | |
| 3134120 | 4/1984 | Fed. Rep. of Germany . | |
| 3504616 | 8/1985 | Fed. Rep. of Germany . | |
| 8706912.1 | 9/1987 | Fed. Rep. of Germany . | |
| 1051847 | 9/1953 | France | 128/92 YL |
| 1239266 | 7/1960 | France | 128/92 YL |
| 2268507 | 4/1975 | France . | |
| 2509167 | 1/1983 | France | 128/92 YL |
| 610518 | 6/1978 | U.S.S.R. . | |

OTHER PUBLICATIONS

Zimmer Orthopaedic Advertisement, Journal of Bone and Joint Surgery, vol. 51B, No. 3, Aug., 1969.

Primary Examiner—Robert A. Hafer
Assistant Examiner—Kevin G. Rooney
Attorney, Agent, or Firm—Peter C. Richardson; Lawrence C. Akers; Elizabeth O. Slade

[57] ABSTRACT

An extendable bone plate is provided. The bone plate (which can be quite small) features two plate portions which are longitudinally displaceable relative to each other. The bone plate preferably includes screw holes for bone screws and gear means between the plate portions adapted to adjust the relative positions of the plate portions. The plate portions have guide portions which are longitudinally slidable within a guide member. At least one of the guide portions includes a rack; and a gear or pinion is rotatably supported within the guide member engaged by the rack, the gear or pinion having tool-engaging surfaces.

13 Claims, 1 Drawing Sheet

BONE PLATE

BACKGROUND OF THE INVENTION

The invention refers to a bone plate, particularly to a small bone plate.

Usually bone plates are designed to stabilize fractural segments and to facilitate the growing together of the bone in the fracture area. It is known to build a bone plate of two parts adapted to follow a change in the length of the bone. A change of length for example may occur by a compression of the fractural segments which for example may be carried out with a specific compression device which is for example known from the German patent specifications 38 202 or 31 34 120. A change of length can also occur caused by a sintering process in the fractural region occurs or with bones of adolescent patients. It is for example known to provide two telescopically engaged bone plates with toothed portions in order to adjust a predetermined plate length. It is also known from the German patent specification 31 34 120 to locate gear means between associated plate portions for the compression of fractural bone segments. The gear means is arranged in a housing on a first plate while the output shaft of the gear means cooperates with the second plate which can be attached to the bone through a bone screw, the bone screw being inserted through an elongated hole of the first plate. Such compression means may be suitable for fractures of limbs, however, in connection with smaller bone plates, particularly in case of applications wherein a small cover of soft tissue exists, e.g. in the face or the like, the known device is not appropriate.

It is also known from the German patent specification 35 04 616 to adjust a clamping means by a threaded spindle relative to a fixedly supported clamping means. Such a device can be applied only externally, thus, cannot be applied to the facial skeleton.

Hence the object of the invention is to provide a bone plate which permits an extension or a contraction, respectively. also with smaller bone plates.

Said object is solved by the features of the claimed invention.

Satisfactorily operating small bone plates are for example known from the German utility model 87 06 912. Above all, they are designed for the application to fractures of the cranial and facial skeleton and for small fractural segments of other skeleton portions. In the known small bone plates, so-called screw hole boundaries are connected to webs, preferably at least a part of the webs having a cross-sectional surface which is equal to or smaller than twice the cross-sectional surface of the screw hole boundary. The relatively thin plates are such dimensioned that they are adapted to be deformed by the surgeon in order to conform to the bone in the region of application. It is intended to avoid a noticeable deformation of the screw hole boundaries when the plate is bent in the plane. For this, it is advantageous if the radius of a transition from the web to the screw hole boundary is dimensioned to be very small.

The bone plate according to the invention is particularly suited for the small bone plate mentioned above. The application of the invention, however, is not restricted thereto.

SUMMARY OF THE INVENTION

In the invention, the associated guide portions of the plate portions are longitudinally displaceably guided in a guide member. At least one of the guide portions includes a gear segment or rack which engages a gear or pinion rotatably supported in the guide member. The pinion includes tool engagement means so that it can be rotated by a rotational tool. Preferably according to an embodiment of the invention each plate portion has a rack, the racks coacting with diametrically opposed portions of the pinion. By this, the pinion shaft is not subjected to single acting bending forces. The bearing for the gear shaft can be designed relatively simple. A double rack engagement has the further advantage that the adjustment path can be doubled. Therefore, only a relatively small rotation of the gear leads to a corresponding adjustment path. It is understood that the path length depends on the diameter of the gear.

DESCRIPTION OF THE PREFERRED EMBODIMENTS

The bone plate according to the invention can be designed relatively flat so that it can be applied internally and also where only a small covering by soft tissue is existing. The guide member for example can be designed as relatively flat housing, the guide channel in the housing having only a depth which is sufficient to receive the gear or the rack portions of the plate portions, respectively. The tool engaging means for a rotating tool can for example be provided by an inner hexagon of the gear shaft. An adjustment of the bone plate according to the invention can be made at relatively short time intervals without unduly troubling the patient. The bone plate according to the invention is preferably used for extension purposes, e.g. for osteotomies.

The bone plate according to the invention can be made very small. The guide member may have a width of 10 mm. Its thickness can be about 3 mm. The plate itself can have a thickness of only about 0.7 mm.

According to a particularly preferred embodiment of the invention the guide portions include two parallel legs, the legs of both guide portions being telescopically inserted one into the other, the outer edge of the outer legs being guided by the associated internal wall of the guide housing. By this, an effective support of the guide portions of the plate portions within the guide housing can be achieved insuring that a clamping during a displacement due to single acting tension or compression forces is avoided.

The guide member or the guide housing, respectively, according to a further embodiment of the invention may be provided with a scale, a mark at the gear or the gear shaft, respectively, cooperating with the scale in order to indicate the rotational angle or the adjusted path, for example upon an extension.

In order to avoid a backward displacement after an extension or a contraction under internally effecting forces suitably set means have to be provided. For example, a set screw can be provided securing the plate portion against the movement relative to each other. Alternatively, the gear shaft or the gear itself can be fixed in each position by a set screw.

A further modification for securing the gear against rotation comprises a gear shaft having an external thread onto which a counternut is screwed adapted to engage the associated surface of the guide member or guide housing, respectively. This nut for example can be formed of a sleeve which for example has hexagonal surfaces on its external surface. The releasing of the set nut and the rotation of the gear, respectively, requires two different wrench surfaces. For this a combined tool can be used which for example comprises a rod having wrench surfaces for the internal hexagon of the gear shaft which rod being telescopically displaceable in a sleeve having a head with internal wrench surfaces. For the removing or the tightening of the counternut the wrench sleeve is slightly slided beyond the wrench rod for engagement with the counternut. The wrench rod itself engages the internal hexagon of the gear shaft. After the counternut is relieved, a corresponding rotation can be carried out by the wrench rod.

It is preferred to recognize the angle of rotation since this angle of rotation is proportional to the adjustment path. For example, a scale can be provided on the wrench sleeve which for example is held firm during rotation of the gear while a mark on the wrench rod moves relative to the scale in order to make the angle of rotation visible.

BRIEF DESCRIPTION OF THE DRAWINGS

The invention will be now explained in greater detail with reference to the accompanying drawings.

Figure 1:
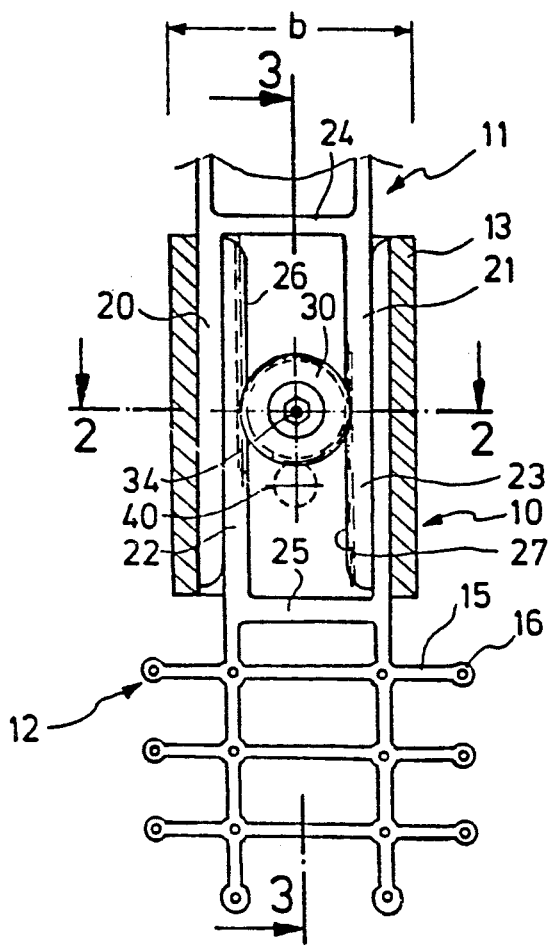
FIG. 1 shows enlarged a plan view and partially a cross section of a bone plate according to the invention.

Before describing the details illustrated in the drawings, it is premised that every described feature is of significance to the invention per se or in conjunction with features of the claims.

The drawings are only diagrammetrical and not in scale.

DETAILED DESCRIPTION OF THE DRAWINGS

The bone plate shown in the FIGS. 1 to 3 comprises a housing 10 guiding plate portions 11, 12 in a manner to be described later. The housing 10 comprises a bottom portion 13 U-shaped in cross section and a plate-like lid portion 14, the portions may be attached to each other by soldering, welding or the like. The height h of the housing for example is about 3 mm. Its width b is for example about 10 mm.

The area of the plate portions 11, 12 beyond the housing 10 is conventionally designed. It consists of strip-like webs 15 which interconnect hole boundaries 16 adapted to receive small bone screws. The webs 15 are dimensioned such that the bone plate can be conformed to the surface contour of a bone by a manual deformation. The portion of the plate portions 11, 12 cooperating with housing 10 is U-shaped and includes legs 20, 21 and 22, 23, respectively. The legs 20, 21 and 22, 23, respectively, are interconnected by transverse webs 24 and 25, respectively. Each outer leg 20, 23, respectively, of the plate portions 11, 12 lies against the inner wall of the housing as can be seen in the FIGS. 1 and 2. The inner edges of the legs 20, 23 are engaged by the other legs 22, 21, respectively. The latter are formed as racks having a toothing 26, 27.

A gear 30 is located between the bottom of bottom portion 13 and lid 14 of the housing, the gear being rotatably supported by a shaft portion 31 within an opening 32 of lid 14. The shaft portion 31 as can be seen in FIG. 1 is configured to fit within an internal hexagon 34 provided in the gear 30. The gear 30 engages on diametrically opposing points the toothing 26, 27 of legs 22, 21. In the position shown in FIG. 1 the plate portions 11, 12 are telescopically placed one into the other as most as possible. If gear 30 is rotated in anti-clockwise direction, the plate portions 11, 12 are displaced away from each other, the double displacement of the plate portions 11, 12 leads to a double displacement path if compared with a displacement where only a single toothing is cooperating with gear 30.

Not shown fixing means, e.g. a set screw, cooperating with the legs of the guide portions of plate portions 11, 12 or with the gear 30 or the gear shaft 31 take care for a securing of the plate portions in each position adjusted.

Figure 3:
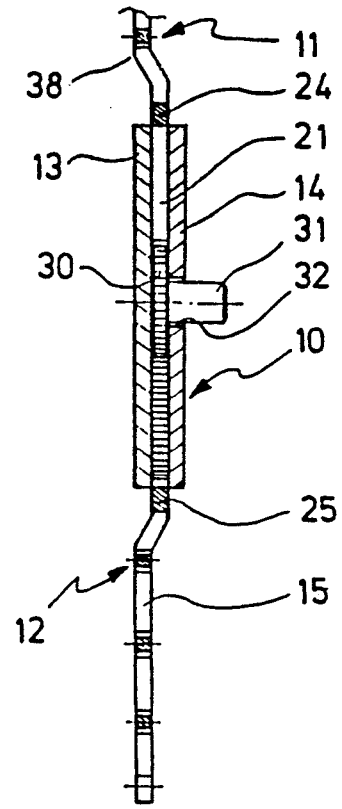
FIG. 3 shows a cross section through the bone plate of FIG. 1 along line 3—3.

As can be seen in FIG. 3, the external parts of the plate portions are offset relative to the guide portions within the housing 10. This is achieved by a cranking as is indicated in FIG. 3 at 38. Thus, the lower side of the external plate portions are aligned with the lower side of housing 10.

In the embodiment shown, the transverse webs 24, 25 and the legs of the guide portions are connected with the external plate portions through two webs. It is understood that deviating constructional alternatives can be selected.

If the transmission ratio between gear 30 and the gear racks 21, 22 is too large, for example a further pinion can be provided as indicated by dotted lines at 40 in FIG. 1. In this case, the gear shaft 31 is not associated with gear 30 but with pinion 40. By this, a corresponding gear reduction can be achieved in order to obtain a small adjustment of the plates 11, 12 upon a relative large angle of rotation.

Figure 2:
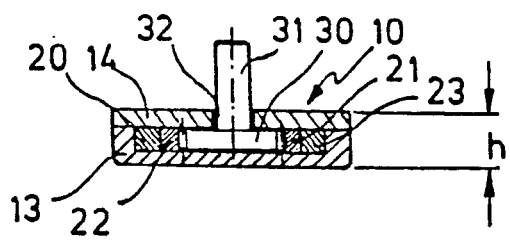
FIG. 2 shows a cross section through the bone plate of FIG. 1 along line 2—2.
Figure 4:
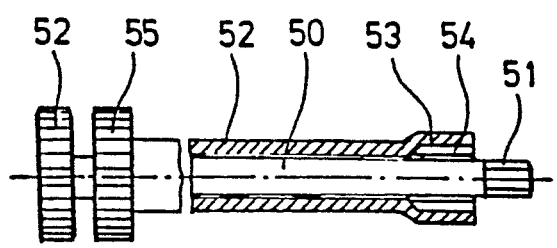
FIG. 4 shows partially in cross section a tool for the adjustment of the bone plate according to FIGS. 1 to 3.
Figure 5:
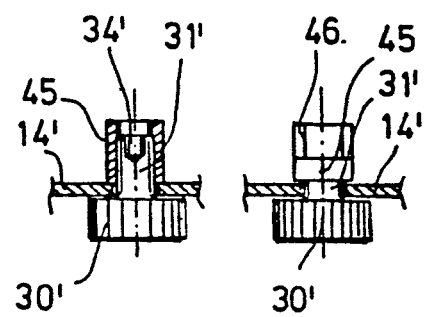
FIG. 5 shows different illustrations of the gear including a set nut.

In FIG. 5 a gear 30' is shown which corresponds to gear 30 of FIGS. 1 to 3. Its shaft 31' has an external thread onto which a threaded sleeve 45 is screwed. The threaded sleeve 45 has an external hexagon 46. The shaft 31' has an internal hexagon 34'. As can be seen, the sleeve 45 serves to fix shaft 31' and thus gear 30' in a predetermined position if the sleeve 45 engages the outer surface of the lid portion 14' of the guide housing not shown. If the sleeve 45 is untightened, the gear 30' can be rotated by means of a respective tool. Such a tool is shown in FIG. 4 by way of example. A wrench rod 50 has hexagonal surfaces 41 at one end thereof which for example can engage the internal hexagon 34 or 34'. At the other end of the wrench rod 50 a knurled knob 52 is formed. A wrench sleeve 53 is slidably positioned on the wrench rod 50, the sleeve 53 having a head 53 including internal hexagonal wrench surfaces 54, a knurled knob 55 being positioned at the other end of the sleeve 53. The wrench head 53 can for example cooperate with the external hexagon 56 of the set sleeve 45. By means of the combination tool of FIG. 4, an adjustment of gear 30' and an actuation of the set sleeve 45 can be carried out subsequently. The knob 45 can be provided with a scale not shown, a mark on knob 52 can be associated with the scale in order to make visible the rotation of gear 30' in form of angle degrees or the linear adjustment path of plates 11, 12.

We claim:

1. A bone plate suitable for internal use on a portion of a human body where only a small cover of soft tissue exists, said bone plate permitting both extension and contraction and comprising:

(a) a first plate portion and a second plate portion longitudinally displaceable relative to each other and including screw holes for bone screws, and (b) gear means located between said first plate portion and said second plate portion and adapted to adjust the relative position of said first plate portion and said second plate portion, and (c) a guide member in the shape of a substantially flat housing, wherein said first plate portion has a first guide portion comprising a first set of parallel legs and said second plate portion has a second guide portion comprising a second set of parallel legs, wherein said first set of parallel legs are telescopically insertable into said second set of parallel legs, wherein said second set of parallel legs have outer edges which are longitudinally slidable within and contact and are guided by said guide member, wherein at least one item selected from the group consisting of said first guide portion and said second guide portion includes a rack, wherein said gear means or pinion is rotatably supported within said guide member and is engaged by said rack, and wherein said gear means or pinion has tool-engaging surfaces.

2. The bone plate of claim 1, wherein said first set of parallel legs includes said rack and wherein said gear means is located interior to said first set of parallel legs.

3. The bone plate of claim 2, wherein said housing has a channel-like housing portion which is covered by a plate-like housing portion.

4. The bone plate of claim 1, wherein said first guide portion and said second guide portion include a first rack and a second rack, respectively, which racks engage said gear means on diametrically opposed locations.

5. The bone plate of claim 2 wherein said plate portions adjacent said guide member are such that the lower side of each plate portion is approximately aligned with the lower side of said guide member.

6. The bone plate of claim 2 comprising at least a further gear means, wherein said further gear means is rotatably supported in said guide member and engages said first gear means, and wherein said further gear means has a smaller diameter than said first gear means and includes tool-engaging surfaces for a rotating tool.

7. The bone plate of claim 2, wherein said gear means has a hexagonal surface located within said gear means and suitable for engagement by a hexagonal wrench.

8. The bone plate of claim 2, wherein said gear means is associated with a fixing member which fixed said gear means in a selected position.

9. The bone plate of claim 2, wherein said gear means has a gear shaft having an external thread onto which a counternut is screwed and said counternut is adapted to be turned against a surface of said guide member.

10. The bone plate of claim 9, wherein a sleeve-like counternut is provided having tool-engaging surfaces for a tool.

11. The bone plate of claim 7, wherein said gear shaft and said counternut are shaped such that a sleeve-like first wrench for said counternut is slidably displaceable on a rod-like second wrench for said hexagonal surface.

12. The bone plate of claim 11, wherein said guide member has a scale on its outer surface and said gear means has a mark associated with said scale.

13. The bone plate of claim 11, and including also a first wrench which includes a scale for cooperation with said guide means and including also a second wrench which bears a mark which cooperates with said scale.

* * * * *